US009490038B2

(12) United States Patent
Wakasaya et al.

(10) Patent No.: US 9,490,038 B2
(45) Date of Patent: Nov. 8, 2016

(54) X-RAY OPTICAL COMPONENT DEVICE AND X-RAY ANALYZER

(71) Applicant: RIGAKU CORPORATION, Akishima-shi (JP)

(72) Inventors: Kenji Wakasaya, Akishima (JP); Tetsuya Ozawa, Hino (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 276 days.

(21) Appl. No.: 14/381,267

(22) PCT Filed: Dec. 12, 2013

(86) PCT No.: PCT/JP2013/083332
§ 371 (c)(1),
(2) Date: Aug. 27, 2014

(87) PCT Pub. No.: WO2014/171037
PCT Pub. Date: Oct. 23, 2014

(65) Prior Publication Data
US 2015/0098547 A1    Apr. 9, 2015

(30) Foreign Application Priority Data

Apr. 17, 2013  (JP) ................................. 2013-086305

(51) Int. Cl.
*G21K 1/06* (2006.01)
*G21K 1/00* (2006.01)
*G01N 23/083* (2006.01)

(52) U.S. Cl.
CPC ............... *G21K 1/00* (2013.01); *G01N 23/083* (2013.01); *G21K 1/06* (2013.01)

(58) Field of Classification Search
CPC ......... G21K 1/00; G21K 1/06; G01N 23/083
USPC .............................. 378/70–91, 114, 115, 117
See application file for complete search history.

(56) References Cited

U.S. PATENT DOCUMENTS 6,528,904 B1    3/2003  Wong

FOREIGN PATENT DOCUMENTS

| JP | 1-1586643 A | 6/1989 |
| JP | 2007-94975 A | 4/2007 |
| JP | 2008-57989 A | 3/2008 |
| WO | WO 2008/142742 A1 | 11/2008 |

*Primary Examiner* — Courtney Thomas
(74) *Attorney, Agent, or Firm* — Buchanan Ingersoll & Rooney PC

(57) ABSTRACT

An X-ray optical component device having an X-ray optical component unit, a motor controller, and a connector. The connector has motor pins and motor terminals electrically connected to a motor when engaged with each other, and a signal pin and signal terminal for sensing detachment of the connector, the signal pin and signal terminal being capable of engaging with each other. A pin-side connector and a terminal-side connector are detachable. When the pin-side connector is detached from the terminal-side connector, the time that the signal pin is removed from the signal terminal is earlier than the time that the motor pins are removed from the motor terminals. During replacement of an X-ray optical component unit equipped with a motor for adjusting the position of an X-ray optical component, unwanted movement of the position of the X-ray optical component provided in the unit is prevented.

9 Claims, 9 Drawing Sheets

X-RAY OPTICAL COMPONENT DEVICE AND X-RAY ANALYZER

TECHNICAL FIELD

The present invention relates to an X-ray optical component device in which an X-ray optical component such as a monochromator or the like is connected to a controller by a connector. The present invention also relates to an X-ray analyzer that uses the X-ray optical component device.

BACKGROUND ART

The apparatus disclosed in Patent Citation 1 is known as a conventional X-ray analyzer that uses an X-ray optical component device. A slit, a monochromator, or the like is cited as an example of the X-ray optical component in this X-ray analyzer. In Patent Citation 1, a unit referred to as a box, an adapter, or the like is used as an X-ray optical component unit provided with the X-ray optical component. A configuration is adopted in which an X-ray optical component unit such as a box, and adapter, or the like is mounted to and dismounted from a goniometer, which is an angle measuring device.

Various types of X-ray optical component units are prepared according to the type of X-ray optical components built into the X-ray optical component unit in the X-ray analyzer, and when a specific measurement is to be made, an X-ray optical component unit that is suitable for the type of measurement is selected from among the various types of X-ray optical component units and mounted to the goniometer. When the type of measurement is changed, the X-ray optical component unit is replaced with a different X-ray optical component unit.

In the actual X-ray analyzer disclosed in Patent Citation 1, an electric wire cable is extended from the X-ray optical component unit, a controller for controlling the operation of components in the X-ray optical component unit is provided in the proper location in the goniometer, and the controller and the electric wire cable extending from the X-ray optical component unit are electrically connected by a connector.

When an X-ray optical component unit is to be replaced with a different X-ray optical component unit, an operation is performed in which the connector belonging to the X-ray optical component unit that is to be replaced is detached from the controller, the X-ray optical component unit is detached from the goniometer, a new X-ray optical component unit is mounted to the goniometer, and the connector belonging to the new X-ray optical component unit is connected to the controller.

In the connector, an electrical connection between instruments is generally accomplished by insertion of a plurality of pins into a plurality of terminals. In the connector used in the X-ray analyzer disclosed in Patent Citation 1, the plurality of pins are of equal length, and the distal ends of the pins are at the same position. The plurality of terminals are also of equal length, and the distal ends of the terminals are at the same position.

Incidentally, a motor (e.g., a stepping motor) for moving the X-ray optical component to adjust the position thereof inside the X-ray optical component unit is sometimes provided separately from the X-ray optical component. When the distal ends of the plurality of pins and the plurality of terminals are at the same position as described above in a case in which a motor is provided inside the X-ray optical component unit in the manner described above, when the connector is detached in a state in which the motor is being controlled to a stationary state, a problem occurs whereby a counter-electromotive force and a surge current (i.e., a current that fluctuates sharply in a short time) cause an output shaft of the motor to rotate, despite the need for the motor to be stopped. In some cases, a control circuit controlling the motor is also damaged.

Patent Citation 2 discloses hot swapping by forming a connector from long pins and short pins. Patent Citation 2 also proposes a circuit configuration for preventing malfunctioning during live insertion and live removal. Hot swapping is a technique that enables a connector of one constituent unit of a device to be disconnected from the device as a whole without interrupting a power supply to the device as a whole. However, Patent Citation 2 does not go so far as to relate and apply the technique of hot swapping to operation of a motor when the motor is provided in a constituent unit.

Patent Citation 3 discloses an insertion/removal detection device for detecting insertion and removal of an external storage device used in an electronic instrument into and from a connector. Specifically, a device is disclosed in which safe insertion/removal is made possible by improving a circuit configuration pertaining to the external storage device, rather than by improving a mechanical configuration relating to the connector. However, Patent Citation 3 also does not go so far as to relate and apply the technique of hot swapping to operation of a motor when the motor is provided in a constituent unit.

Patent Citation 4 discloses a system provided with a constituent component capable of hot swapping. Specifically, a hot swapping technique is realized using a connector having long pins and short pins. However, Patent Citation 4 also does not go so far as to relate and apply the technique of hot swapping to operation of a motor when the motor is provided in a constituent unit.

CITATION LIST

Patent Literature

Patent Citation 1: JP2008-057989A
Patent Citation 2: JP2007-094975A
Patent Citation 3: WO2008/142742
Patent Citation 4: U.S. Pat. No. 6,528,904
Patent Citation 5: JPH01-156643A

SUMMARY OF INVENTION

Technical Problem

The present invention was developed in view of the abovementioned problems of the conventional apparatus, and the objects of the present invention are to make it possible to replace various types of X-ray optical component units without interrupting the power supply to the apparatus as a whole, and, during replacement of an X-ray optical component unit that is equipped with a motor for adjusting the position of the X-ray optical component, to prevent an unintended shift in the position of the X-ray optical component provided in the unit.

Solution to Problem

The X-ray optical component device according to the present invention has: an X-ray optical component unit provided with an X-ray optical component and a motor for moving the position of the X-ray optical component; a motor controller for controlling operation of the motor; and a connector for electrically connecting the X-ray optical component unit and the motor controller; wherein the connector has: a motor pin and a motor terminal electrically connected to the motor in a state of engagement with each other; and a signal pin and a signal terminal for sensing detachment of the connector, the signal pin and signal terminal being capable of engaging with each other; the connector is capable of attaining a connected state in which the motor pin is inserted in the motor terminal and the signal pin is inserted in the signal terminal, and a non-connected state in which the motor pin is removed from the motor terminal and the signal pin is removed from the signal terminal; and the time that the signal pin is removed from the signal terminal is earlier than the time that the motor pin is removed from the motor terminal when the connector is detached from the connected state to the non-connected state.

Through this X-ray optical component device, when the connector is detached, since electrical contact between the signal pin and the signal terminal is disengaged earlier than the electrical contact between the motor pin and the motor terminal is disengaged, the supply of electric power to the motor can be stopped by controlling a power feed path rather than by interrupting an electric power supply wire before the emergence of a counter-electromotive force or a surge current from the motor. An unwanted change in the position of the X-ray optical component (e.g., mirror) due to counter-electromotive force is thereby prevented, and adverse effects such as damage to internal circuits by surge currents are prevented.

In the X-ray optical component device according to the present invention, the distal-end position of the signal pin may be set back toward the rear relative to the distal-end position of the motor pin, or the distal-end position of the signal terminal may be set back toward the rear relative to the distal-end position of the motor terminal.

In the X-ray optical component device according to the present invention, the motor controller can supply electric power to the motor via the connector when the connector is in the connected state, the motor controller can sense removal of the signal pin from the signal terminal, and when the motor controller senses that the signal pin has been removed from the signal terminal, the motor controller performs a control for stopping the supply of electric power to the motor before the motor pin is removed from the motor terminal.

In the X-ray optical component device according to the present invention, the motor controller may have a motor drive circuit including a transistor. The control for stopping the supply of electric power to the motor may comprise closing a gate of the transistor.

The X-ray optical component device according to the present invention may further have an eccentric cam fixed to an output shaft of the motor, a movable member fixed to the X-ray optical component and contacting a cam face of the eccentric cam, and an elastic urging member for pressing the movable member against the cam face by elastic force. The eccentric cam may be rotated by rotation of the output shaft of the motor, the movable member may be moved by the rotation of the eccentric cam, and the position of the X-ray optical component may be adjusted by the movement of the movable member.

The mechanism described above which uses the eccentric cam, the movable member, and the elastic urging member is a so-called sine-bar mechanism. A sine-bar mechanism is disclosed in Patent Citation 5, for example. In a sine-bar mechanism, since the movable member moves in the radial direction with respect to the output shaft rather than in a thrust direction of the output shaft of the motor, when the X-ray optical component unit is detached from the X-ray analyzer, the position of the X-ray optical component can be securely maintained the same as during the detachment, even while the X-ray optical component unit is the detached state.

The X-ray analyzer according to the present invention has an X-ray source for generating X-rays incident on a specimen, an X-ray detection means for detecting X-rays exiting from the specimen, and the X-ray optical component device including an X-ray optical component disposed on an X-ray optical path from the X-ray source to the X-ray detection means, and the X-ray optical component device is configured from an X-ray optical component device having the various structures described above.

Advantageous Effects of Invention

Through the X-ray optical component device according to the present invention, when the connector is detached, since electrical contact between the signal pin and the signal terminal is disengaged earlier than the electrical contact between the motor pin and the motor terminal is disengaged, the supply of electric power to the motor can be stopped by controlling a power feed path rather than by interrupting an electric power supply wire before the emergence of a counter-electromotive force or a surge current from the motor. It is thereby possible to prevent an unwanted change in the position of the X-ray optical component (e.g., mirror) due to counter-electromotive force, and to prevent adverse effects such as damage to internal circuits by surge currents.

REFERENCE SIGNS LIST

Figure 1:
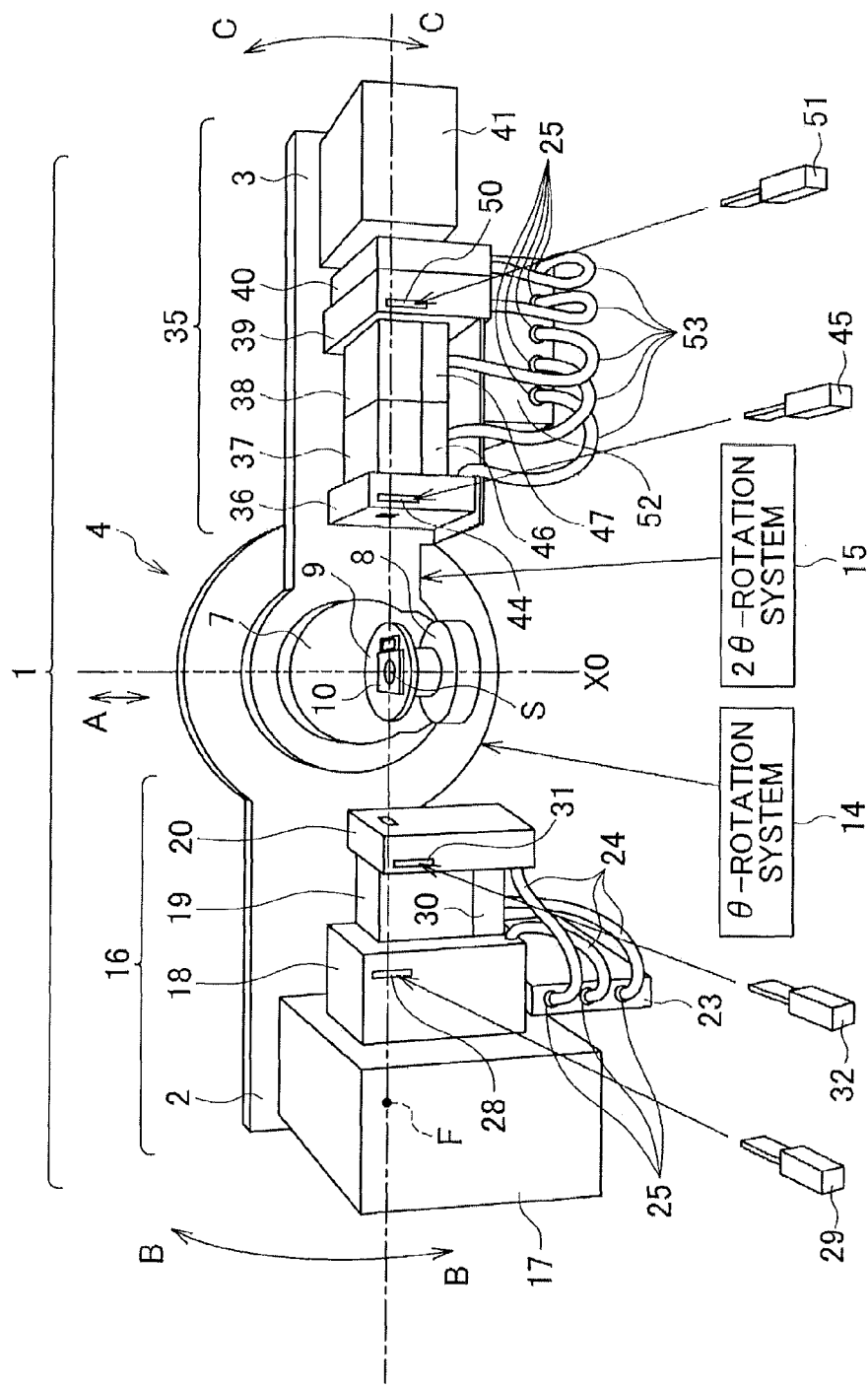
FIG. 1 is a view showing an embodiment of the X-ray optical component device and X-ray analyzer according to the present invention.

1.X-ray analyzer, 2.incidence-side arm, 3.receiving-side arm, 4.goniometer, 7.Z-axis stage, 8.specimen support, 9.specimen plate, 10.specimen holder, 11.vertical driving device, 14.θ-rotation system, 15.2θ-rotation system, 16.incident optical system, 17.X-ray tube, 18.CBO unit, 19.incidence-side first optical element, 20.incident slit box, 23.interface board, 24.electric wire cable, 25.connector, 25a.pin-side connector, 25b.terminal-side connector, 28.slit insertion opening, 29.selection slit, 30.element base, 31.slit insertion opening, 32.longitudinal limiting slit, 35.receiving optical system, 36.first receiving slit box, 37.receiving-side second optical element, 38.receiving-side third optical element, 39.second receiving slit box, 40.attenuator box, 41.X-ray detector, 44.slit insertion opening, 45.Kβ filter, 46.ROD adapter, 47.RPS adapter, 50.slit insertion opening, 51.height limiting slit, 52.interface board, 53.electric wire cable, 56.multilayer mirror, 57.motor, 57a.output shaft, 57b.stator, 57c.rotor, 58.eccentric cam, 58a.cam face, 59.movable member, 60.compression spring (elastic urging member), 61.line, 63.motor controller, 64.receiving slit, 65.terminal, 66.coil, 67.driver, 68.drive control circuit, 69.wiring, 72.gate, d. distance, F.X-ray focus (X-ray source), K1~K6.stator coil terminals, P11~P44.pins, S. specimen, T11~T44.terminals, Tr1~Tr4.switching circuits, V0,V1.voltage, X0.specimen central axis

DESCRIPTION OF EMBODIMENTS

The X-ray optical component device and X-ray analyzer according to the present invention are described below on the basis of embodiments. The present invention is, of course, not limited to these embodiments. In the drawing accompanying the present specification, constituent elements are sometimes shown at a scale that is different from the actual scale thereof in order to facilitate understanding of characteristic portions.

Figure 2:
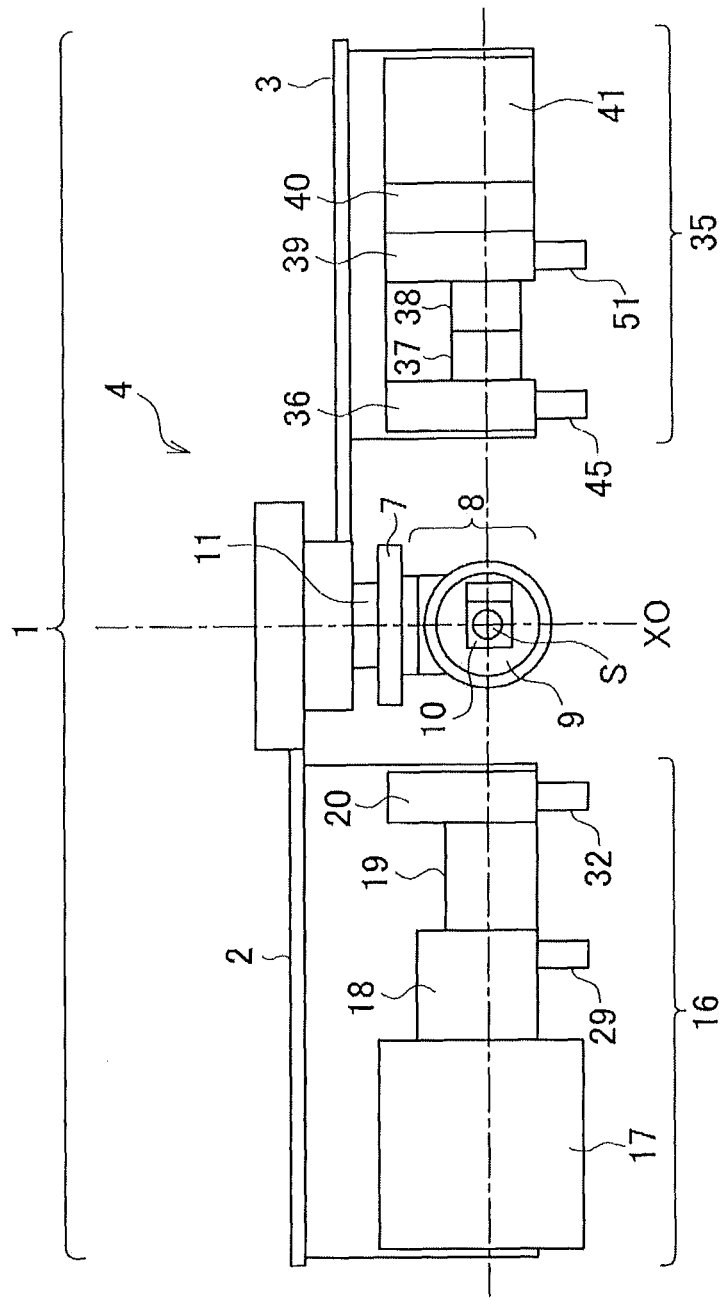
FIG. 2 is a plan view of the X-ray analyzer shown in FIG. 1.

FIGS. 1 and 2 chow an embodiment of the X-ray analyzer according to the present invention. The X-ray analyzer 1 shown herein has a goniometer (angle measuring device) 4 having an incidence-side arm 2 and a receiving-side arm 3. A Z-axis stage 7 is attached to a center portion of the goniometer 4. A specimen support 8 is attached to the Z-axis stage 7. A specimen plate 9 is attached to the specimen support 8. A specimen S as a measurement subject is filled into a specimen holder 10. The specimen holder 10 is placed on the specimen plate 9. The Z-axis stage 7, the specimen support 8, the specimen plate 9, and the specimen holder 10 are each an attachment.

A vertical driving device 11 (see FIG. 2) is additionally provided to the Z-axis stage 7. The Z-axis stage 7 is moved in the vertical direction (the vertical direction indicated by the arrow A in FIG. 1; the direction through the paper surface in FIG. 2) by the vertical driving device 11, and the position of the specimen S in the vertical direction can thereby be adjusted. Specifically, the Z-axis stage 7 functions as a specimen vertical position adjustment unit for adjusting the vertical position of the specimen S.

In the present embodiment, the Z-axis stage 7, the specimen support 8, the specimen plate 9, and the specimen holder 10 are cited as examples of attachments. However, various other elements may also be attachments. For example, a sample changer, a specimen oscillation mechanism, or the like is possible as another attachment.

A θ-rotation system 14 is connected to the incidence-side arm 2. A 2θ-rotation system 15 is connected to the receiving-side arm 3. The incidence-side arm 2 is driven by the θ-rotation system 14, and rotationally moves as indicated by the arrow B-B about a specimen central axis X0 which is a horizontal axis passing through a surface of the specimen S. The receiving-side arm 3 is driven by the 2θ rotation system 15, and rotationally moves as indicated by the arrow C-C about the specimen central axis X0.

The θ-rotation system 14 and the 2θ-rotation system 15 may be configured from a rotational drive structure having any structure. In the present embodiment, rotation systems are employed in which a rotation-angle-controllable motor, e.g., a servo motor, a pulse motor, or the like, is used as a motive power source, and the motive power thereof is transmitted to each arm via a powertrain comprising a worm and a worm wheel.

(Incident Optical System)

The incidence-side arm 2 supports an incident optical system 16. The incident optical system 16 has an X-ray tube 17, a cross beam optics (CBO) unit 18, an incidence-side first optical element 19, and an incident slit box 20. The X-ray tube 17 has inside thereof an X-ray focus F as an X-ray source. The CBO unit 18, the incidence-side first optical element 19, and the incident slit box 20 each function as an X-ray optical component unit.

(CBO Unit)

Figure 3:
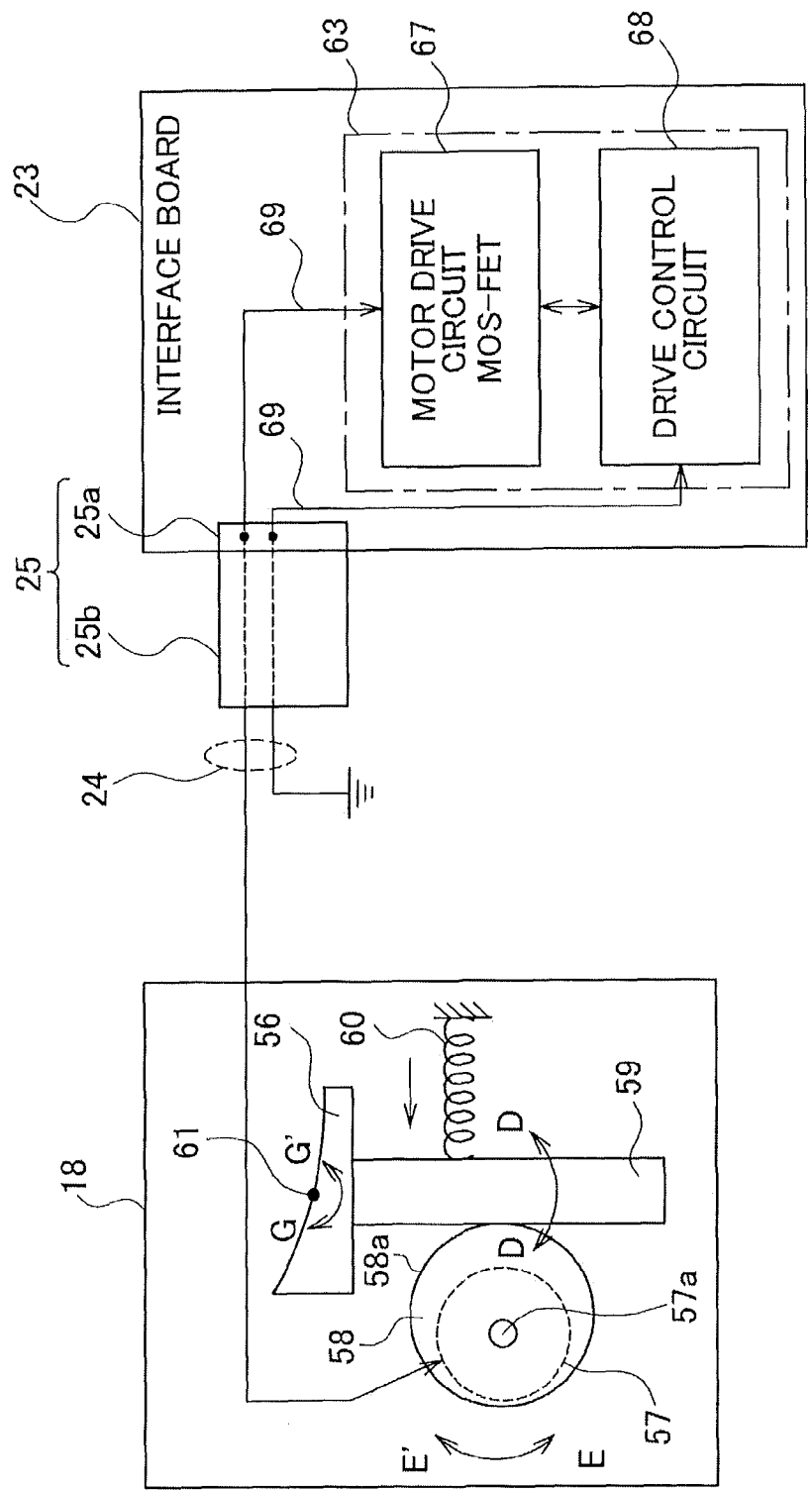
FIG. 3 is a view showing an embodiment of the X-ray optical component device according to the present invention.

The CBO unit 18 is a unit for forming X-rays having an intensity and cross-sectional shape corresponding to each type of measurement (e.g., powder measurement, small-angle scattering measurement, micro-part measurement, in-plane measurement, and the like). As shown in FIG. 3, the CBO unit 18 has inside thereof a multilayer mirror 56 as an X-ray optical component. A motor 57 for adjusting the position of the multilayer mirror 56 is also built into the CBO unit 18.

An eccentric cam 58 is fixed to an output shaft 57a of the motor 57. A movable member 59 extending from the multilayer mirror 56 is pressed against an external peripheral face of the eccentric cam 58, i.e., a cam face 58a, by the spring force (i.e., elastic force) of a compression spring 60 as an elastic urging member. The movable member 59 is round column shaped, round tube shaped, polygonal column shaped, square tube shaped, or flat plate shaped. The movable member 59 can pivot as indicated by the arrow D-D about a line 61 extending in the direction through the paper surface of FIG. 3 through the center of an X-ray reflecting face of the multilayer mirror 56. By rotating the output shaft 57a of the motor 57 clockwise or counterclockwise as indicated by the arrow E-E', the multilayer mirror 56 integrated with the movable member 59 can be rotatably pivoted as indicated by the arrow G-G' in order to adjust the position thereof. The pivoting mechanism described above which uses the eccentric cam 58, the movable member 59, and the compression spring 60 is sometimes referred to as a sine-bar mechanism.

A motor controller 63 for controlling the rotation of the output shaft 57a of the motor 57 is built into an interface board 23. The motor controller 63 has a driver (i.e., motor drive circuit) 67 for driving the motor 57, and a drive control circuit 68 formed by a microcomputer. The motor 57 and the driver 67 in the motor controller 63 are connected by an electric wire cable 24 and wiring 69. The drive control circuit 68 in the motor controller 63 is connected to a voltage of 0V, for example, by the electric wire cable 24 and the wiring 69. The electric wire cable 24 and the interface board 23 are connected by a connector 25. The mechanical configuration of the electric wire cable 24, the connector 25, and the interface board 23 in the present embodiment is as shown in the lower part of the incidence side (left side) of the X-ray analysis 1 apparatus in FIG. 1.

The CBO unit 18 also has a slit insertion opening 28. A selection slit 29 can be inserted in the slit insertion opening 28. The inserted selection slit 29 is thus positioned on the X-ray emission side of the multilayer mirror.

The following four types of slits, for example, are included as components that can serve as the selection slit 29.

(1) Selection slit BB
(2) Selection slit PB
(3) Selection slit SA
(4) Selection slit MA Here, BB is a slit for a focusing method, PB is a slit for a parallel beam method, SA is a slit for small-angle scattering measurement, and MA is a slit for micro-part measurement. The selection slit SA is obtained by narrowing the slit width of the selection slit PB. The selection slit MA is obtained by decreasing the length of the selection slit PB. A hollow block is also sometimes disposed instead of the CBO unit 18 at the location where the CBO unit 18 is attached. Such a hollow block is sometimes referred to as an incidence path.

(Incidence-Side First Optical Element)

The incidence-side first optical element 19 is detachably attached on an element base 30. The following X-ray optical elements, for example, are applied as the incidence-side first optical element 19.
(1) Two-crystal monochromator Ge (220)×2
(2) Two-crystal monochromator Ge (400)×2
(3) Four-crystal monochromator Ge (220)×4
(4) Four-crystal monochromator Ge (400)×4
(5) Soller slit Open
(6) Soller slit 5 deg
(7) Soller slit 2.5 deg
(8) In-plane parallel slit collimator (PSC) 1.0 deg
(9) In-plane PSC 0.5 deg
(10) In-plane PSC 0.15 deg The monochromator is directly attached on the element base 30. The soller slit and in-plane PSC are attached to the monochromator attached on the element base 30, or are attached to the element base 30 via a dedicated incident parallel slit (IPS) adapter. A monochromator, soller slit, or PSC is sometimes not provided at the location where the incidence-side first optical element 19 is attached. An IPS adapter is also sometimes not attached.

(Incident Slit Box)

The incident slit box 20 has a slit insertion opening 31. A longitudinal limiting slit 32 may be inserted in the slit insertion opening 31. The following slits, for example, are included as components that can serve as the longitudinal limiting slit 32.
(1) Longitudinal limiting slit 0.5 mm
(2) Longitudinal limiting slit 2 mm
(3) Longitudinal limiting slit 5 mm
(4) Longitudinal limiting slit 10 mm
(5) Longitudinal limiting slit 15 mm A motor for opening and closing the slit is built into the incident slit box 20. A driver for controlling the rotation of an output shaft of the motor is built into the interface board 23. The motor and the driver in the board 23 are connected by the electric wire cable 24. The electric wire cable 24 and the interface board 23 are connected by the connector 25.

In the present embodiment, a method whereby a label affixed in an appropriate location on the first optical element 19 is sensed by a sensor, e.g., a light sensor, provided in an appropriate location on the first optical element 19 is used to sense the type name of the first optical element 19 attached on the element base 30. The element base 30 and the interface board 23 are linked by the electric wire cable 24 in order to transfer the output signal of the sensor, and the output signal of the light sensor on the element base 30 is outputted to the outside through the electric wire cable 24 and the board 23.

(Receiving Optical System)

In FIG. 1, the receiving-side arm 3 supports a receiving optical system 35. The receiving optical system 35 has a first receiving slit box 36, a receiving-side second optical element 37, a receiving-side third optical element 38, a second receiving slit box 39, an attenuator box 40, and an X-ray detector 41. The first receiving slit box 36, the receiving-side second optical element 37, the receiving-side third optical element 38, the second receiving slit box 39, and the attenuator box 40 each function as an X-ray optical component unit.

(First Receiving Slit Box)

Figure 4:
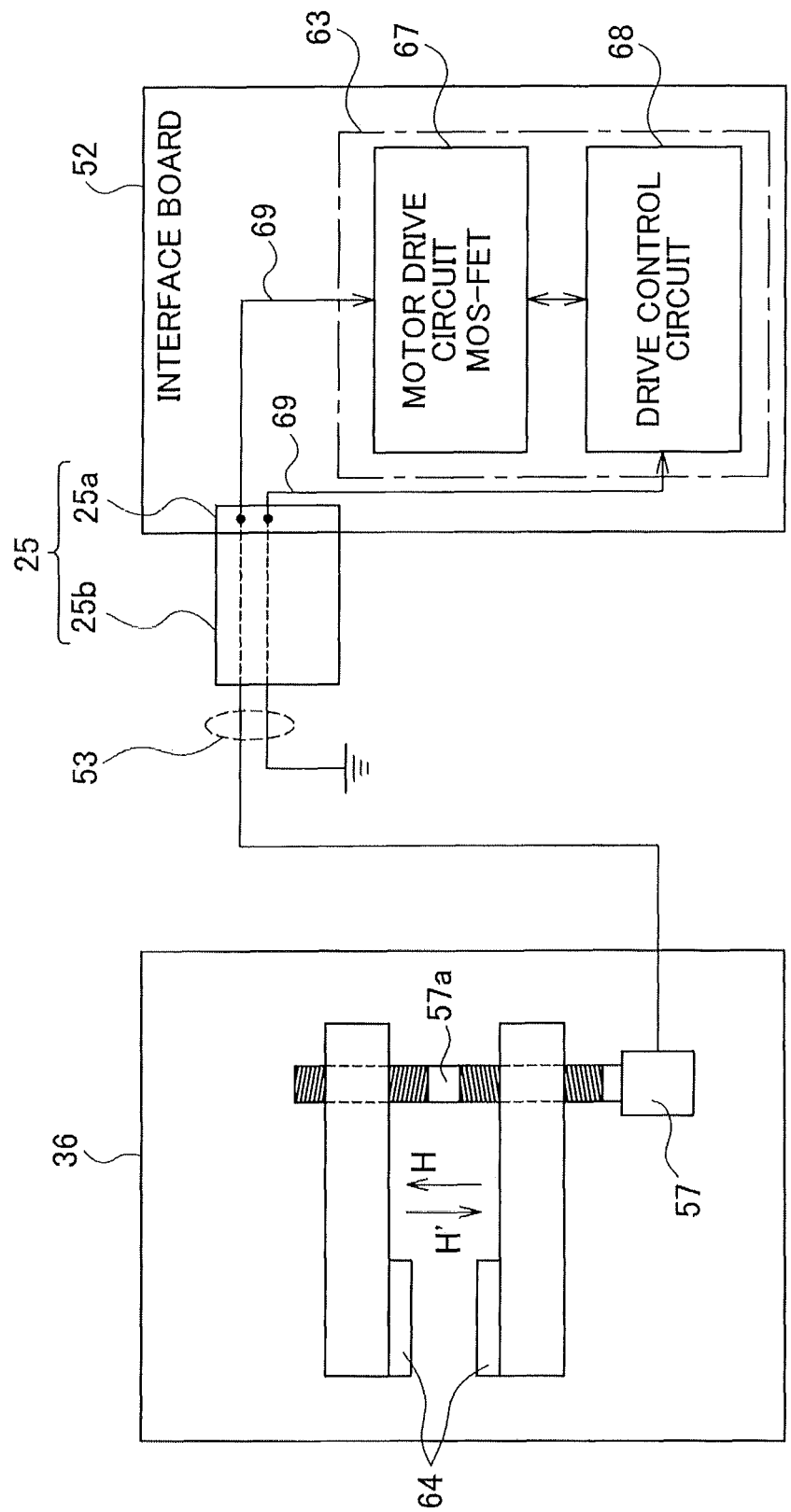
FIG. 4 is a view showing another embodiment of the X-ray optical component device according to the present invention.

As shown in FIG. 4, for example, the first receiving slit box 36 is equipped with a receiving slit 64 as an X-ray optical component and the motor 57 for opening and closing the slit. The output shaft 57a of the motor 57 is engaged with the receiving slit 64. The output shaft 57a of the motor 57 is rotated clockwise or counterclockwise about the central axis thereof, and can thereby open and close the receiving slit 64 as indicated by the arrows H-H'. The sine-bar mechanism shown in FIG. 3 may be used as the mechanism for opening and closing the receiving slit 64.

The motor controller 63 for controlling the rotation of the output shaft 57a of the motor 57 is built into an interface board 52. The motor controller 63 has the driver 67 for driving the motor 57, and the drive control circuit 68 formed by a microcomputer. The motor 57 and the driver 67 in the motor controller 63 are connected by an electric wire cable 53 and wiring 69. The drive control circuit 68 in the motor controller 63 is connected to a voltage of 0 V, for example, by the electric wire cable 53 and the wiring 69. The electric wire cable 53 and the interface board 52 are connected by the connector 25. The mechanical configuration of the electric wire cable 53, the connector 25, and the interface board 52 in the present embodiment is as shown in the lower part of the receiving side (right side) of the X-ray analyzer in FIG. 1.

The first receiving slit box 36 also has a slit insertion opening 44. A Kβ filter 45 can be inserted in the slit insertion opening 44.

(Receiving-Side Second Optical Element)

The receiving-side second optical element 37 is detachably attached on a ROD adapter (receiving optical device adapter) 46. The following X-ray optical elements, for example, are applied as the receiving-side second optical element 37.
(1) Parallel slit analyzer (PSA) open
(2) PSA 1.0 deg
(3) PSA 0.5 deg
(4) PSA 0.114 deg
(5) PSA 0.05 deg
(6) Vacuum path A PSA may also not be attached on the ROD adapter 46, leaving a vacancy.

(Receiving-Side Third Optical Element)

The receiving-side third optical element 38 is detachably attached on an RPS adapter (receiving parallel slit adapter) 47. The following X-ray optical elements, for example, are applied as the receiving-side third optical element 38.
(1) Soller slit 5 deg
(2) Soller list 2.5 deg
(3) In-plane parallel slit analyzer (PSA) 1.0 deg
(4) In-plane PSA 0.5 deg
(5) In-plane PSA 0.114 deg The RPS adapter 47 itself is sometimes not provided. The soller slit or in-plane PSA may also not be attached on the RPS adapter 47, leaving a vacancy.

(Second Receiving Slit Box)

A receiving slit is provided inside the second receiving slit box 39. A motor for opening and closing the slit is also provided inside the second receiving slit box 39. The configuration shown in FIG. 4 may be used as the configuration that uses this receiving slit and motor. The sine-bar mechanism shown in FIG. 3 may be employed as the mechanism for opening and closing the receiving slit.

A slit insertion opening 50 is also provided to the second receiving slit box 39. A height limiting slit 51 may be inserted in the slit insertion opening 50. The height limiting slit 51 is also sometimes not inserted in the slit insertion opening 50.

(Attenuator Box)

An attenuator is provided inside the attenuator box 40. A motor for switching the type of attenuator is also provided inside the attenuator box 40.

In the present embodiment, a method whereby a label is sensed by a light sensor is used to sense what type of second optical element 37 is attached on the ROD adapter 46, and to sense what type of third optical element 38 is attached on the RPS adapter 47. Therefore, the ROD adapter 46 and the board 52 are linked by the electric wire cable 53, the RPS adapter 47 and the board 52 are linked by the electric wire cable 53, and the output signals of the light sensors on the adapters 46, 47 are outputted to the outside through the electric wire cable 53 and the board 52.

A signal input/output wire not shown in the drawings is furthermore connected to each of the interface board 23, the θ-rotation system 14, the 2θ-rotation system 15, and the interface board 52. The signal input/output wires are connected to a controller formed by a microcomputer, for example. This controller is furthermore connected to a personal computer, for example.

(Measurement Classification)

In the present embodiment, various types of measurements can be performed in the X-ray analyzer 1 by appropriately replacing the X-ray optical component unit (i.e., the CBO unit 18, incidence-side first optical element 19, incident slit box 20, first receiving slit box 36, receiving-side second optical element 37, receiving-side third optical element 38, second receiving slit box 39, attenuator box 40, etc.). For example, focusing method measurement, reflectance measurement, small-angle scattering measurement, micro-part measurement, and various other types of measurement can be performed.

By replacing the X-ray optical component unit in order to perform these measurements, the X-ray optical component therein is replaced, and the optimum optical system is configured. When focusing method measurement, reflectance measurement, and small-angle scattering measurement, for example, are to be performed, the X-ray optical components shown in the table below are selectively used in the X-ray analyzer 1 shown in FIG. 1.

(1) Measurement classification=Simple wide-angle measurement (focusing method), Specimen=Powder specimen loaded onto glass specimen plate

| | At time of optical system adjustment | At time of specimen position adjustment | At time of data measurement |
|---|---|---|---|
| CBO selection slit 29 | BB | BB | BB |
| First optical element 19 (crystal monochromator) | None | None | None |
| First optical element 19 (incident parallel slit) | Soller slit 5.0 deg | Soller slit 5.0 deg | Soller slit 5.0 deg |
| Longitudinal limiting slit 32 | 10 mm | 10 mm | 10 mm |
| Filter 45 | None | None | None |
| Second optical element 37 (Parallel slit analyzer) | PSA open | PSA open | PSA ope |
| Third optical element 38 (receiving parallel slit) | Soller slit 5.0 deg | Soller slit 5.0 deg | Soller slit 5.0 deg |
| Height limiting slit 51 | None | None | None |
| Attenuator 40 | None | None | None |

(2) Measurement classification=Reflectance measurement (high resolution), Specimen=1 cm×1 cm thin-film specimen

| | At time of optical system adjustment | At time of specimen position adjustment | At time of data measurement |
|---|---|---|---|
| CBO selection slit 29 | PB | PB | PB |
| First optical element 19 (crystal monochromator) | Ge (220) × 2 | Ge (220) × 2 | Ge (220) × 2 |
| First optical element 19 (incident parallel slit) | Soller slit open | Soller slit open | Soller slit open |
| Longitudinal limiting slit 32 | 10 mm | 5 mm | 5 mm |
| Filter 45 | None | None | None |
| Second optical element 37 (Parallel slit analyzer) | PSA open | PSA open | PSA open |
| Third optical element 38 (receiving parallel slit) | Soller slit open | Soller slit open | Soller slit open |
| Height limiting slit 51 | None | None | None |
| Attenuator 40 | None | None | None |

(3) Measurement classification=Transmission small-angle scattering measurement, Specimen=Nanoparticles enclosed in capillary

| | At time of optical system adjustment | At time of specimen position adjustment | At time of data measurement |
|---|---|---|---|
| CBO selection slit 29 | SA | SA | SA |
| First optical element 19 (crystal monochromator) | None | None | None |
| First optical element 19 (incident parallel slit) | Soller slit 5.0 deg | Soller slit 5.0 deg | Soller slit 5.0 deg |
| Longitudinal limiting slit 32 | 10 mm | 10 mm | 10 mm |
| Filter 45 | None | None | None |
| Second optical element 37 (Parallel slit analyzer) | Vacuum path | Vacuum path | Vacuum path |

-continued

|  | At time of optical system adjustment | At time of specimen position adjustment | At time of data measurement |
|---|---|---|---|
| Third optical element 38 (receiving parallel slit) | None | None | None |
| Height limiting slit 51 | None | None | None |
| Attenuator 40 | None | None | None |

As shown in FIGS. 1 and 3, in the present embodiment, the CBO unit 18, the incidence-side first optical element 19, and the incident slit box 20, each of which function as the X-ray optical component unit, are connected to the interface board 23 via the electric wire cable 24 and the connector 25, respectively. As shown in FIGS. 1 and 4, the first receiving slit box 36, the receiving-side second optical element 37, the receiving-side third optical element 38, the second receiving slit box 39, and the attenuator box 40, each of which function as the receiving-side X-ray optical component unit, are connected to the interface board 52 via the electric wire cable 53 and the connector 25.

Figure 5A:
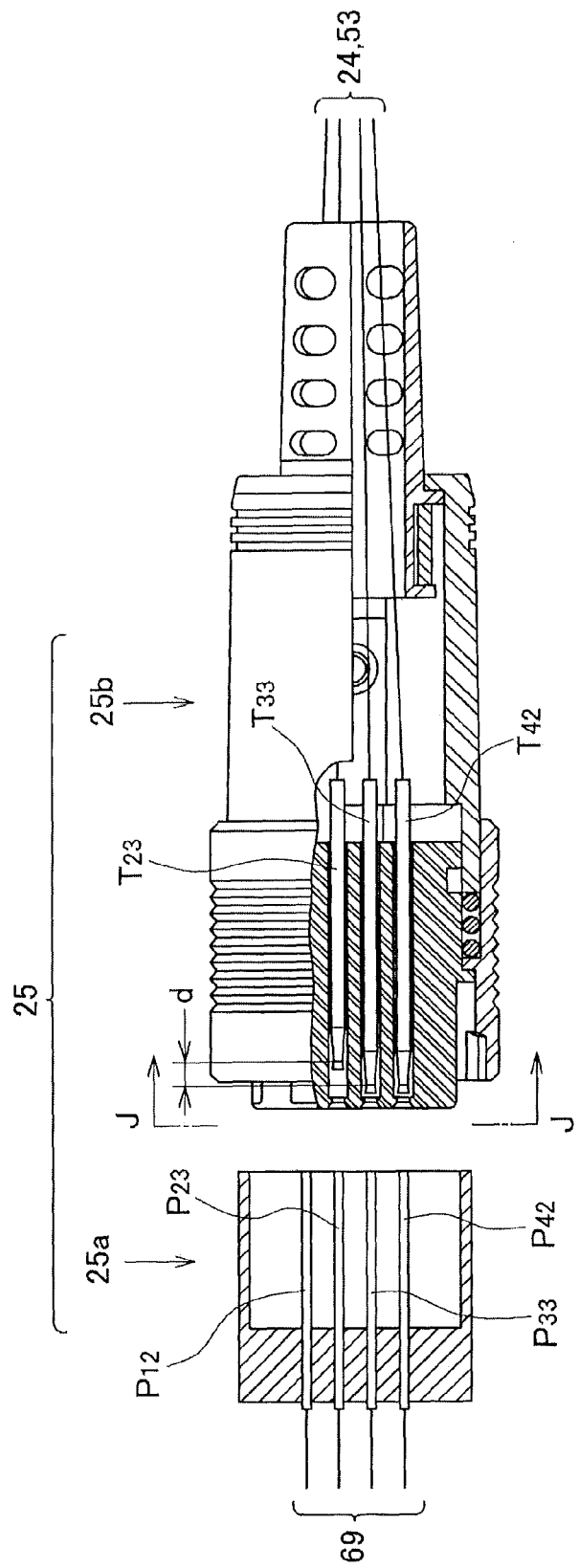
FIG. 5A is a partial cut-away side view of the whole of an embodiment of the connector, which is the main part of FIGS. 3 and 4.
Figure 5B:
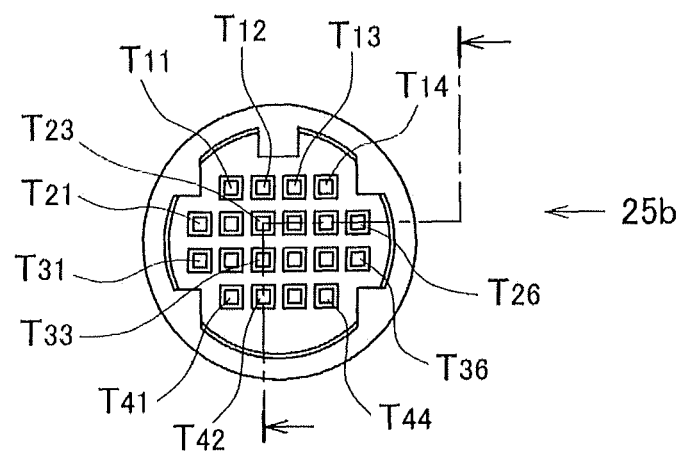
FIG. 5B is an end face view along line J-J in FIG. 5A.

The connector 25 has the structure shown in FIGS. 5A and 5B. FIG. 5A is a side view in which a portion of the connector 25 is cut away. FIG. 5B is an end face view of the connector 25 along the line J-J in FIG. 5A. In these drawings, the connector 25 is configured from a pin-side connector 25a and a terminal-side connector 25b. As shown in FIGS. 3 and 4, the pin-side connector 25a is attached to the interface board 23, 52, and the terminal-side connector 25b is attached to a distal end of the electric wire cable 24, 53.

In FIG. 5B, a plurality (20 in the present embodiment) of terminals T11 through T44 are provided to an end part on a connection face side of the terminal-side connector 25b. Here, two-digit numerals accompanying the reference symbol T indicate the position of a terminal. For example, T11 indicates the terminal in the first row from the top and the first column from the left in FIG. 5B, and T44 indicates the terminal in the fourth row and fourth column. Pins P11 through P44 in positions corresponding to the terminals T11 through T44, respectively, are also provided to an end part of the pin-side connector 25a on the connection face side thereof. Pins P12, P23, P33, and P42 of the pins are shown in FIG. 5A.

Figure 6:
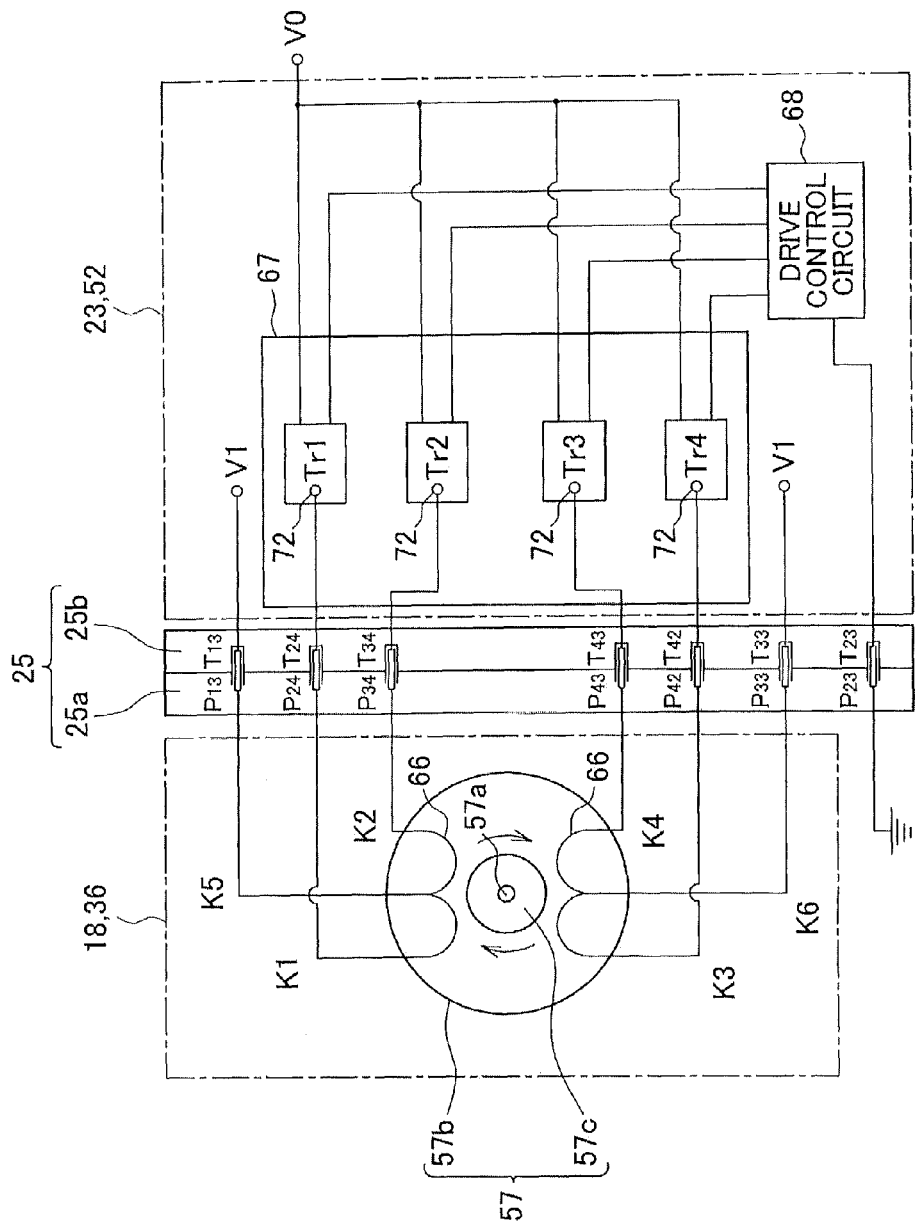
FIG. 6 is a circuit diagram corresponding to the configuration shown in FIGS. 3 and 4.

The motor 57 provided inside the CBO unit 18, which is the X-ray optical component unit in FIG. 3, and the motor 57 provided inside the first receiving slit box 36, which is the X-ray optical component unit in FIG. 4, are formed by pulse motors having a stator 57b and a rotor 57c, as shown in FIG. 6. The output shaft 57a is integrated with the rotor 57c.

A coil 66 for forming a rotating magnetic field, the coil being provided to the stator 57b, has six input terminals K1 through K6, and the terminals are connected to the six pins P24, P34, P42, P43, P13, and P33, respectively. Pins that are connected to the motor 57 are referred to hereinafter as motor pins.

The driver 67 provided in the interface board 23 in FIG. 3 has four switching circuits Tr1 through Tr4 each including a transistor, as shown in FIG. 6. The switching circuits Tr1 through Tr4 each have a gate 72, and the gates 72 are connected to terminals T24, T34, T43, T42, respectively, of the terminal-side connector 25b. The switching circuits Tr1 through Tr4 transmit a motor drive voltage V0 to the terminals T24, T34, T43, T42 through the gates 72 in accordance with an instruction from the drive control circuit 68.

Middle terminals K5, K6 of the stator coil 66 are connected to a motor drive voltage V1 via the terminals T13, T33 and the pins P13, P33, respectively, of the connector 25. The switching circuits Tr1 through Tr4 connect the motor drive voltage V1 to the voltage V0 through the gates 72 from the stator coil 66 via a junction between pins P24, P34 and terminals T24, T34, and a junction between P43, P42 and terminals T43, T42 of the connector 25 in accordance with an instruction from the drive control circuit 68. By this connection, a motor drive current flows to the motor 57. The terminals T13, T24, T34, T43, T42, T33, and so on connected to the motor 57 are referred to hereinafter as motor terminals.

The length of the terminal T23 in the center region of the connection face of the terminal-side connector 25b in FIG. 5B is reduced as shown in FIG. 5A, and the distal-end position thereof is thereby set back toward the rear a distance d from the distal-end positions of the other terminals. This distance d is about 1.4 mm, for example. The distal-end position of the pin P23 inserted in the terminal T23 is the same as the distal-end position of the other pins. The pin P23 and the terminal T23 are for sensing whether the connector 25 is connected or disconnected. Consequently, the pin P23 and the terminal T23 are sometimes referred to as the signal pin P23 and the signal terminal T23 hereinafter.

Since the distal-end position of the signal terminal T23 is set back relative to the other terminals, and the distal-end position of the signal pin P23 is the same as that of the other pins, as described above, when the pin-side connector 25a is put into the terminal-side connector 25b and the pin-side connector 25a and terminal-side connector 25b are connected, connection of the signal pin P23 and the signal terminal T23 is initiated a predetermined time after the initiation of connection between the pins and terminals other than the signal pin P23 and the signal terminal T23.

Meanwhile, when the pin-side connector 25a is detached from the terminal-side connector 25b, the pins and terminals other than the signal pin P23 and the signal terminal T23 are disconnected after a predetermined time has elapsed from disconnection between the signal pin P23 and the signal terminal T23. Actually, a time of about 50 msec to 100 msec is considered to be required for a person to completely unplug the pin-side connector 25a from the terminal-side connector 25b mechanically. A time of about 5 msec is considered to be required for electrical disconnection between all pins and terminals to occur once a person begins to remove the pin-side connector 25a from the terminal-side connector 25b. It is considered to require less than 1 msec for disconnection between the signal pin P23 and the signal terminal T23 to occur once a person begins to remove the pin-side connector 25a from the terminal-side connector 25b.

In FIG. 6, the signal pin P23 is connected to a voltage of 0 V, for example, and the signal terminal T23 is connected to the drive control circuit 68. The drive control circuit 68 recognizes that the connector 25 is in the connected state when the signal pin P23 and the signal terminal T23 are connected, and recognizes that the connector 25 is in the non-connected state when the signal pin P23 and the signal terminal T23 are separated.

In the present embodiment, the pins P13, P24, P34, P43, P42, P33 belonging to the motor 57 and the pins other than the signal pin P23, and the terminals T13, T24, T34, T43, T42, T33 belonging to the motor 57 and the terminals other than the signal terminal T23 are used for applications other than motor control. These other applications include transfer of signals from a sensor for sensing the position of X-ray optical components such as the mirror, the monochromator, slits, and the like, for example.

Figure 7A:
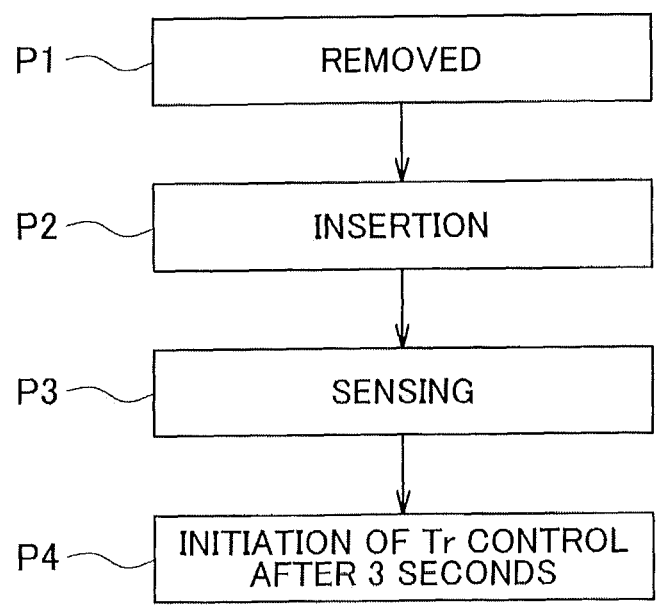
FIG. 7A is a process diagram showing operations performed using the X-ray analyzer of FIG. 1, and particularly the steps performed during connection of the connector.

Since the present embodiment is configured as described above, during connection of the connector 25, the signal pin P23 and the signal terminal T23 are separated at first, as shown in FIG. 7A, and the drive control circuit 68 therefore recognizes that the connector 25 is in the non-connected state (step P1). A worker then inserts the pin-side connector 25a in the terminal-side connector 25b in FIG. 6 (step P2). When the signal pin P23 is inserted in the signal terminal T23, the drive control circuit 68 senses this insertion (step P3).

The drive control circuit 68 having sensed connection between the signal pin P23 and the signal terminal T23 initiates control of the driver 67 a predetermined time, e.g., three seconds, after sensing this connection (step P4). In this control, the switching circuits Tr1 through Tr4 sequentially turn ON/OFF the gates 72 at a predetermined timing, a rotating magnetic field is thereby formed in the stator 57b of the motor 57, and the rotor 57c (and thus the output shaft 57a) rotates. The position of the multilayer mirror 56 in FIG. 3, for example, is adjusted by this rotation.

Figure 7B:
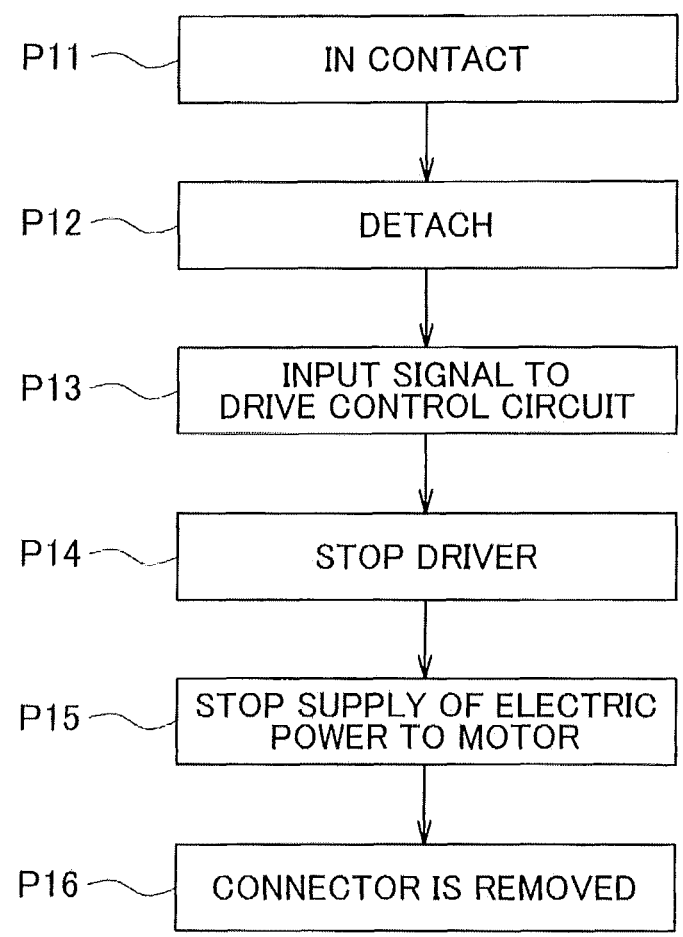
FIG. 7B is a process diagram showing operations performed using the X-ray analyzer of FIG. 1, and particularly the steps performed during disconnection of the connector.

In FIG. 6, during detaching of the connector 25, the drive control circuit 68 recognizes that the connector 25 is at first in a contacting state, as shown in FIG. 7B (step P11). A worker then detaches the pin-side connector 25a from the terminal-side connector 25b (step P12). At this time, contact between the signal pin P23 and the signal terminal T23 is first removed, and a signal (removal signal) indicating the removal of contact arrives at the drive control circuit 68 (step P13). The drive control circuit 68 then stops the driver 67 before contact between the pins and terminals other than the signal pin P23 and the signal terminal T23 is removed (step P14). Specifically, the gates 72 of the switching circuits Tr1 through Tr4 are closed, and the supply of electric power to the stator coils, i.e., the supply of electric power to the motor 57, is stopped (step P15). The pin-side connector 25a is then completely removed mechanically from the terminal-side connector 25b, and a state is attained in which the X-ray optical component units 18, 36, and so on can be replaced (step P16).

Incidentally, in the X-ray analyzer 1 of the present embodiment, an X-ray optical component unit such as the CBO unit 18 or the like is sometimes temporarily detached from the X-ray analyzer 1, and the same X-ray optical component unit is subsequently mounted in the same position of the X-ray analyzer 1 to perform a measurement. In such cases, in the conventional connector in which the positions of the distal ends of the connector pins and connector terminals are the same for all pins and terminals, when the connector is removed, a counter-electromotive force occurs in the motor which flows as a surge current, momentarily causing unwanted movement of the output shaft of the motor by a certain angle.

Therefore, in the conventional X-ray analyzer, the position of the X-ray optical component (e.g., mirror, slit, monochromator, etc.) built into the X-ray optical component unit is offset from the position thereof prior to detachment when the X-ray optical component unit is remounted to the X-ray analyzer. As a result, there is a risk of discrepancy in measurement conditions between a measurement from before the X-ray optical component unit was detached and a measurement from after the same X-ray optical component unit was remounted. Even if the angle offset of the output shaft of the motor is so small as to be less than one degree, in the field of X-ray analysis, such a minute offset is sufficient to significantly affect measurement results. In order to prevent such adverse effects, optical position adjustment must be performed for the X-ray optical component built into the X-ray optical component unit each time the X-ray optical component unit is remounted.

In the conventional X-ray analyzer, there is also a risk of damage to the driver 67 or the drive control circuit 68 when a large surge current flows upon withdrawal of the connector.

Through the present embodiment, in contrast with the conventional configuration, the gates 72 of the switching circuits Tr1 through Tr4 are closed at the time that the signal pin P23 and the signal terminal T23 are removed from each other, and connection between the pins and terminals for the motor 57 is subsequently undone. A counter-electromotive force in the motor 57 or a surge current from the motor 57 therefore no longer occurs. As a result, the position of the X-ray optical component is no longer offset by a counter-electromotive force or the like during detachment and remounting of the X-ray optical component unit. The problem of needing to perform optical adjustment of the X-ray optical component each time the X-ray optical component unit is remounted is therefore overcome.

In the X-ray optical component unit 18 shown in FIG. 3, i.e., the CBO unit 18, the multilayer mirror 56 that is the X-ray optical component is driven by a sine-bar mechanism. Meanwhile, in the X-ray optical component unit 36 shown in FIG. 4, i.e., the first receiving slit box 36, a drive mechanism is employed in which a rotary shaft 57a of the motor 57 is configured as a screw shaft. In the drive mechanism shown in FIG. 4, positional offset in the receiving slit 64 when the supply of electric power to the motor 57 is stopped is considered to be possible due to the effects of instability in the movement of the output shaft 57a in the thrust direction thereof (extension direction of the shaft) and the presence of gear backlash along the thrust direction of the output shaft 57a.

In contrast, when a sine-bar drive mechanism is employed as shown in FIG. 3, since the movable member 59 abuts on the cam face 58a, i.e., abuts on the output shaft 57a from the radial direction, movement of the output shaft 57a of the motor 57 in the thrust direction no longer affects the movement of the multilayer mirror 56, which is the X-ray optical component, and because a gear is not used, the movement of the multilayer mirror 56 is also unaffected by gear backlash. Therefore, almost no positional offset occurs in the multilayer mirror 56 when the supply of electric power to the motor 57 is stopped. As an extremely advantageous result, when the CBO unit 18 is detached from the X-ray analyzer 1, position of the multilayer mirror 56 can be maintained the same as during the detachment, even while the CBO unit 18 is in the detached state.

OTHER EMBODIMENTS

A preferred embodiment of the present invention is described above, but the present invention is not limited to this embodiment and various modifications may be made thereto within the scope of the invention as recited in the claims.

For example, in the embodiment shown in FIG. 6, connector pins P11 through P44 are provided on the X-ray optical component unit 18, 36 side, and connector terminals T11 through T44 are provided on the interface board 23, 52 side. However, this configuration may be reversed, so that the connector terminals T11 through T44 are provided on the X-ray optical component unit 18, 36 side, and the connector pins P11 through P44 are provided on the interface board 23, 52 side.

In the embodiment shown in FIG. 5A, the distal-end position of the signal terminal T23 is set back relative to the other terminals, and the timing of a detachment completion signal (i.e., connection disengagement signal) for this terminal is earlier than that of the detachment completion signals for the other pins and terminals. However, the same operational effects can be obtained by adopting a configuration in which the distal-end position of the signal pin P23 is set back relative to the other pins, instead of setting back the distal-end position of a terminal.

In the embodiment described above, the present invention is applied to an X-ray analyzer 1 that is configured as shown in FIG. 1. However, the present invention may also be applied to an X-ray analyzer having a different configuration from that of the X-ray analyzer 1 shown in FIG. 1.

In the embodiment shown in FIG. 6, the closing of a transistor gate is employed as the method for stopping the supply of electric power to the motor 57. However, the supply of electric power to the motor 57 may be stopped by any other method as needed.

In the embodiment shown in FIG. 5B, the signal terminal T23 is provided substantially at the center of all the terminals T11 through T44. However, the signal terminal T23 may be provided at any position relative to the other terminals.

The invention claimed is:

1. An X-ray optical component device having:
    an X-ray optical component unit provided with an X-ray optical component and a motor for moving the position of the X-ray optical component;
    a motor controller for controlling operation of said motor; and
    a connector for electrically connecting said X-ray optical component unit and said motor controller; wherein
    said connector has:
        a motor pin and a motor terminal electrically connected to said motor in a state of engagement with each other; and
        a signal pin and a signal terminal for sensing detachment of said connector, the signal pin and signal terminal configured to engage each other;
    said connector is configured to attain
        a connected state in which said motor pin is inserted in said motor terminal and said signal pin is inserted in said signal terminal, and
        a non-connected state in which said motor pin is removed from said motor terminal and said signal pin is removed from said signal terminal; and
    the time that said signal pin is removed from said signal terminal is earlier than the time that said motor pin is removed from said motor terminal when said connector is detached from said connected state to said non-connected state.

2. The X-ray optical component device according to claim 1, wherein
    the distal-end position of said signal pin is set back toward the rear relative to the distal-end position of said motor pin, or
    the distal-end position of said signal terminal is set back toward the rear relative to the distal-end position of said motor terminal.

3. The X-ray optical component device according to claim 2, wherein
    said motor controller supplies electric power to said motor via the connector when said connector is in said connected state;
    said motor controller senses removal of said signal pin from said signal terminal; and
    when said motor controller senses that said signal pin has been removed from said signal terminal, said motor controller performs a control for stopping the supply of electric power to said motor before said motor pin is removed from said motor terminal.

4. The X-ray optical component device according to claim 3, wherein
    said motor controller has a motor drive circuit including a transistor; and
    the control for stopping the supply of electric power to said motor comprises closing a gate of said transistor.

5. The X-ray optical component device according to claim 4, having
    an eccentric cam fixed to an output shaft of said motor, a movable member fixed to said X-ray optical component and contacting a cam face of said eccentric cam, and an elastic urging member for pressing the movable member against said cam face by elastic force;
    said eccentric cam being rotated by rotation of the output shaft of said motor, said movable member being moved by the rotation of the eccentric cam, and the position of said X-ray optical component being adjusted by the movement of the movable member.

6. An X-ray analyser having an X-ray source for generating X-rays incident on a specimen, X-ray detection means for detecting X-rays exiting from the specimen, and an X-ray optical component device provided with an X-ray optical component disposed on an X-ray optical path from said X-ray source to said X-ray detection means, wherein
    said X-ray optical component device is the X-ray optical component device according to claim 5.

7. The X-ray optical component device according to claim 1, wherein
    said motor controller supplies electric power to said motor via the connector when said connector is in said connected state;
    said motor controller senses removal of said signal pin from said signal terminal; and
    when said motor controller senses that said signal pin has been removed from said signal terminal, said motor controller performs a control for stopping the supply of electric power to said motor before said motor pin is removed from said motor terminal.

8. The X-ray optical component device according to claim 1, having
    an eccentric cam fixed to an output shaft of said motor, a movable member fixed to said X-ray optical component and contacting a cam face of said eccentric cam, and an elastic urging member for pressing the movable member against said cam face by elastic force;
    said eccentric cam being rotated by rotation of the output shaft of said motor, said movable member being moved by the rotation of the eccentric cam, and the position of said X-ray optical component being adjusted by the movement of the movable member.

9. An X-ray analyser having an X-ray source for generating X-rays incident on a specimen, X-ray detection means for detecting X-rays exiting from the specimen, and an X-ray optical component device provided with an X-ray optical component disposed on an X-ray optical path from said X-ray source to said X-ray detection means, wherein
said X-ray optical component device is the X-ray optical component device according to claim 1.

* * * * *